United States Patent [19]

Selva et al.

[11] Patent Number: 4,782,042

[45] Date of Patent: Nov. 1, 1988

[54] ANTIBIOTIC A 40926 MANNOSYL AGLYCON

[75] Inventors: Enrico Selva, Gropello Cairoli; Beth P. Goldstein, Milan; Pietro Ferrari, Ferriere; Giovanni Cassani, Pavia; Francesco Parenti, Lainate, all of Italy

[73] Assignee: Gruppo Lepetit S.p.A., Milan, Italy

[21] Appl. No.: 945,732

[22] Filed: Dec. 23, 1986

[30] Foreign Application Priority Data

Dec. 30, 1985 [GB] United Kingdom ............... 8531846

[51] Int. Cl.$^4$ ..................... A61K 37/02; C07K 5/12
[52] U.S. Cl. .......................... 514/9; 514/10; 530/317
[58] Field of Search ................... 514/9, 10; 530/317

[56] References Cited

FOREIGN PATENT DOCUMENTS 177882 4/1986 European Pat. Off. .

OTHER PUBLICATIONS

J. Am. Chem. Soc. (1984) 106, 4891–4895, Hunt, et al.
Chem. Abstr., vol. 102 (1985) 113884.
Chem. Abstr., vol. 102 (1985) 6010.
Chem. Abstr., vol. 104 (1986) 6189.
Chem. Abstr., vol. 104 (1986 6190.
Chem. Abstr., vol. 91 (1979) 188229.
J. Williams, J. Amer. Chem. Soc., 106, 4895–4908 (1984).

Primary Examiner—Delbert R. Phillips
Attorney, Agent, or Firm—J. Michael Dixon; Raymond A. McDonald; Stephen L. Nesbitt

[57] ABSTRACT

The present invention concerns a new antibiotic substance denominated antibiotic A 40926 mannosyl aglycon and the addition salts thereof, a process for preparing it from antibiotic A 40926 complex or a factor thereof, and its use in the treatment of infectious disease involving microorganisms susceptible to it.

4 Claims, 3 Drawing Sheets

ANTIBIOTIC A 40926 MANNOSYL AGLYCON

The present invention concerns a new antibiotic substance denominated antibiotic A 40926 mannosyl aglycon and the addition salts thereof, a process for preparing it from antibiotic A 40926 complex or a factor thereof, and its use in the treatment of infectious diseases involving microorganisms susceptible to it.

Antibiotic A 40926 complex and its factors are antibiotic substances active against gram positive bacteria and Neisseriae strains, which are produced by strains of Actinomadura.

An A 40926 producing strain of Actinomadura genus has been deposited on June 8, 1984 with American Type Culture Collection (ATCC)—12301 Parklawn Drive, Rockville, Md. 20852, U.S.A. under the provisions of the Budapest Treaty.

Antibiotic A 40926 is a complex antimicrobial substance; five of its components have been isolated and identified as factor PA, PB, A, B and $B_0$.

Antibiotic A 40926 and its factors, as well as the producing microorganism and the process for their preparation, have been disclosed in European Patent Application Publication No. 177882. On the basis of the physico-chemical data and by reference to the structure of known antibiotic substances, the following formula can be attributed to the A 40926 factors (the numbering is analogous to that proposed by J. Williams in J.A.C.S., 106, 4895–4908 (1984)):

Antibiotic A 40926 factors A and B are mainly transformation products of antibiotic A 40926 factor PA and factor PB respectively, and are often already present in the fermentation broth.

It has been found that antibiotic A 40926 factor PA can be transformed into antibiotic A 40926 factor A and antibiotic A 40926 factor PB can be transformed into antibiotic A 40926 factor B under basic conditions.

As a consequence, when the fermentation broth, or an antibiotic A 40926 containing extract or concentrate thereof, is allowed to stand for a certain time under basic conditions (e.g. aqueous solution of a nucleophilic base, at a pH>9 overnight,) an antibiotic A 40926 complex will be obtained which is enriched in antibiotic A 40926 factor A and factor B.

Figure 1:
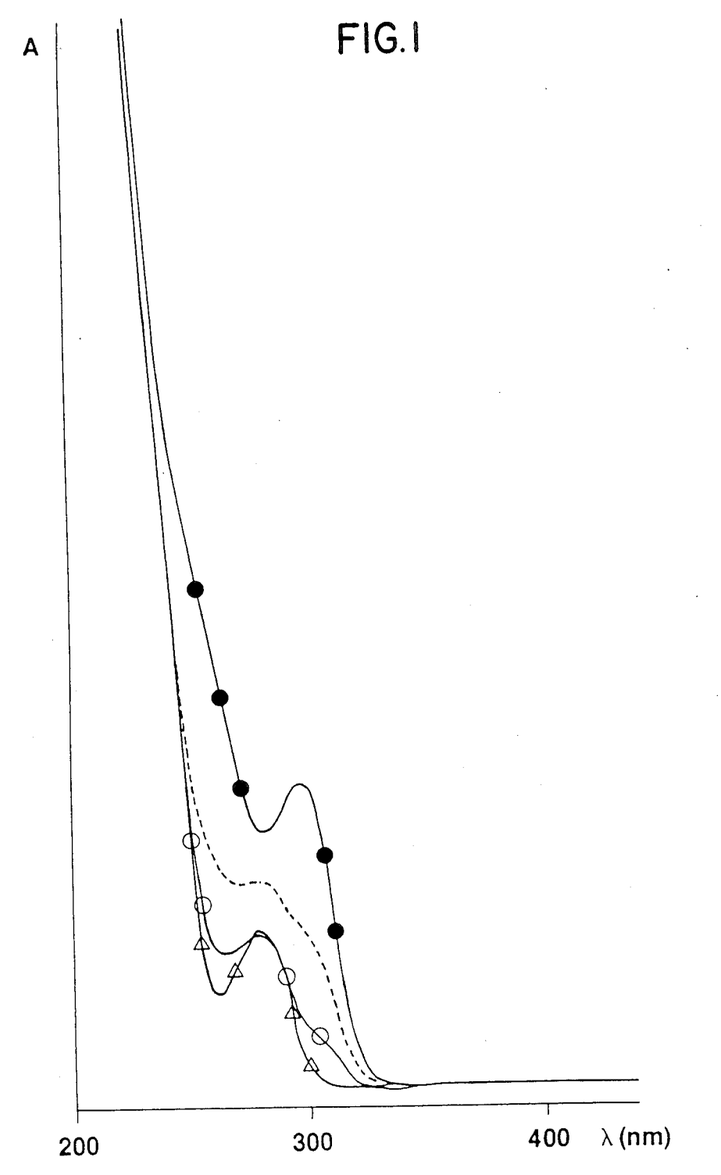

Antibiotic A 40926 mannosyl aglycon has the following characteristics (in the non-addition salt form):

(A) ultraviolet absorption spectrum, which is shown in FIG. 1 of the accompanying/drawings, and exhibits the following absorption maxima:

|     |                           | λ max (nm)     |
|-----|---------------------------|----------------|
| (a) | 0.1 N HCl                 | 280            |
| (b) | phosphate buffer pH 7.38  | 280            |
|     |                           | 300 (shoulder) |
| (c) | 0.1 N potassium hydroxide | 298            |
| (d) | phosphate buffer pH 9.0   | 282            |
|     |                           | 300 (shoulder) |

Figure 2:
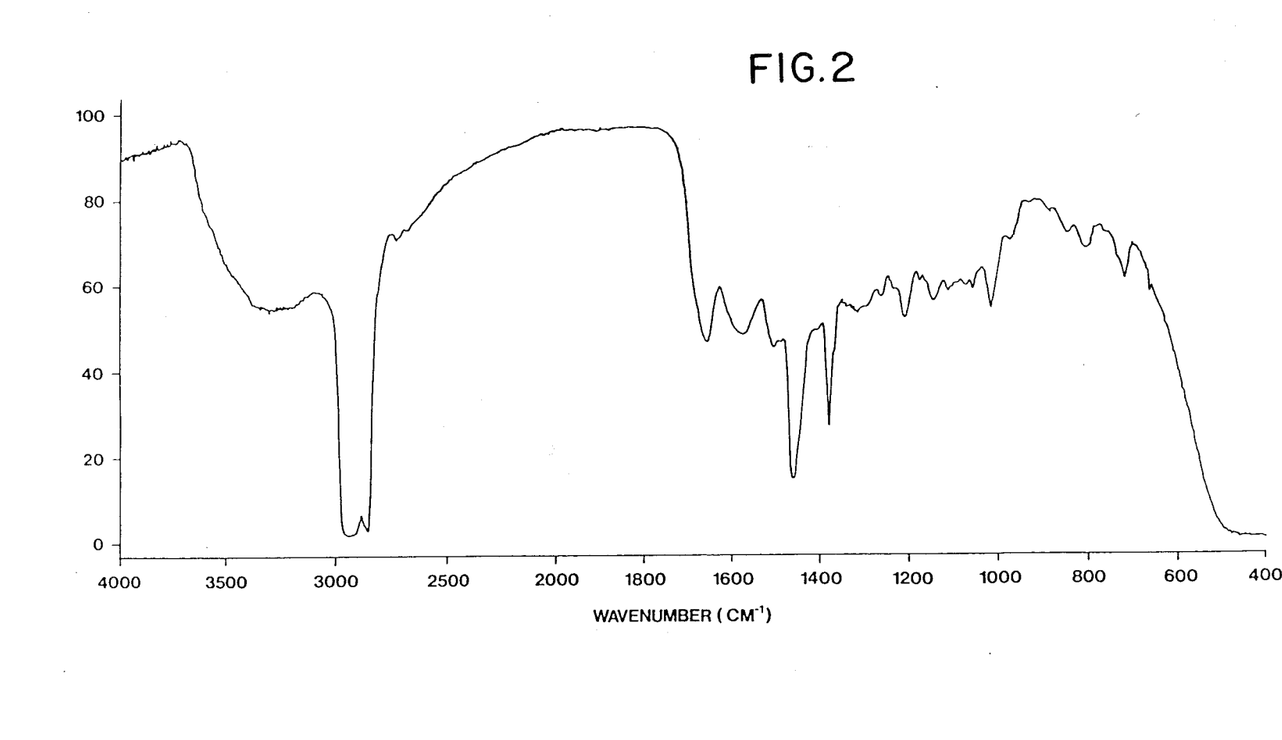

(B) infrared absorption spectrum which is shown in

I wherein
A represents a N-($C_{11}$–$C_{12}$)acyl-aminoglucuronyl group and
B represents a mannosyl or acetylmannosyl group.

More particularly, antibiotic A 40926 factor A is the compound of the above formula wherein A represents undecanoyl-aminoglucuronyl and B represents mannosyl, antibiotic A 40926 factor $B_0$ is the compound of the above formula wherein A represents iso-dodecanoyl-amino-glucuronyl and B represents mannosyl.

Antibiotic A 40926 factor PA and factor PB differ from the corresponding factor A and $B_0$ in that the mannose unit is replaced by an acetyl-mannose unit.

Antibiotic A 40926 factors PA and PB, at least under certain fermentation conditions, are the main antibiotic products of the A 40926 producing microorganism.

FIG. 2 of the accompanying drawings and exhibits the following absorption maxima (cm$^{-1}$): 3700–3100; 3000–2800 (nujol); 1655; 1620–1540; 1505; 1460 (nujol); 1375 (nujol) 1350–1250; 1210; 1150; 1020; 970; 850, 810

Figure 3:
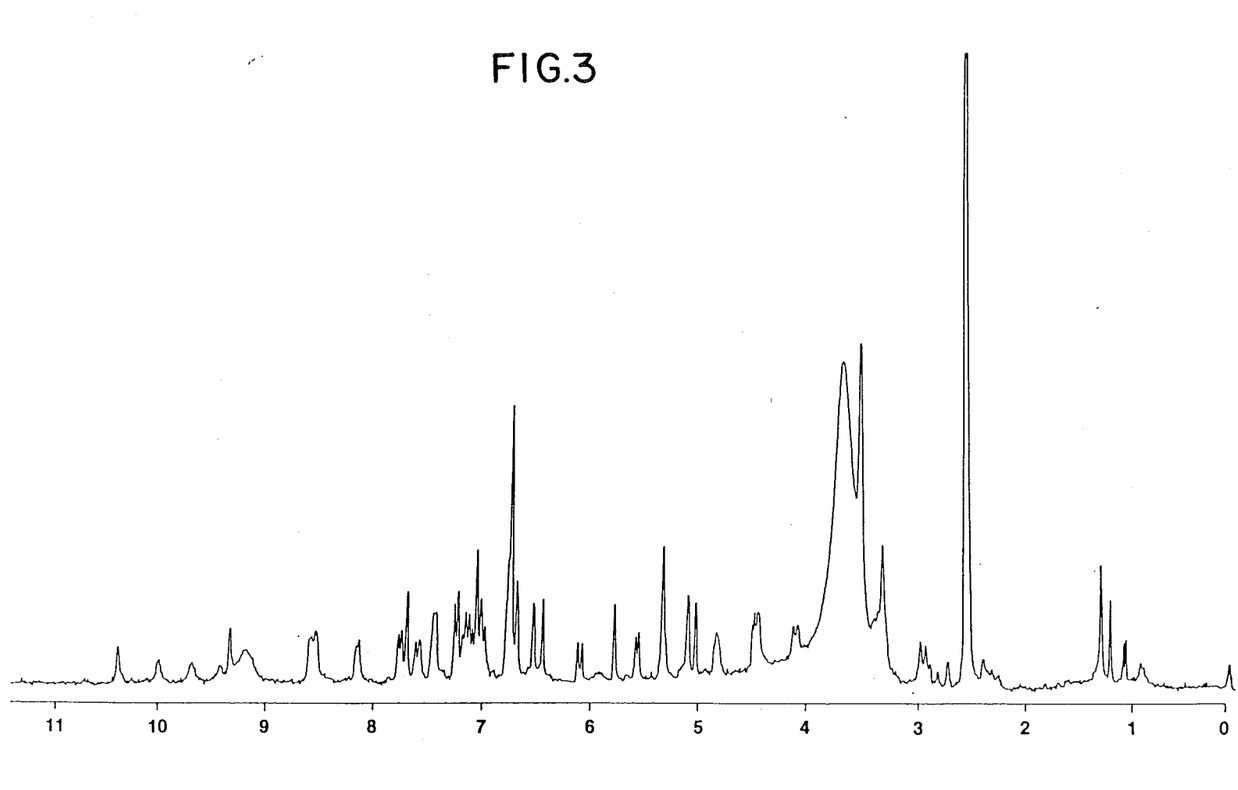

(C) $^1$H-NMR spectrum which is shown in FIG. 3 and exhibits the following groups of signals (in ppm) at 270 MHz recorded in DMSO $d_6$ (hexadeuterodimethylsulfoxide) plus $CF_3COOH$ using TMS as the internal standard (0.00 ppm), (δ=ppm, multiplicity, attributions): 2.51, s (DMSOd$_5$); 2.50, s (NCH$_3$); 2.88, m (Z2); 3.30, m (Z'2); 4.08, m (X6); 4.44, d (X5); 4.49, d (X7); 4.83, m (X2); 5.02, s (4F); 5.08, s (Z6); 5.31, s (anomeric proton of mannose); 5.53 d (X4); 5.78, s (4B); 6008, d (X3); 7.70, s (6B); 6.44–8.52 (aromatic and peptidic NH's)
d=doublet; m=multiplet; s=singlet (D) retention-time ($R_t$) of 1.18 relative to antibiotic L 17054 (TA3-1) ($R_t$=8.78 min), when analyzed by reverse phase HPLC under the following conditions:
  column: Ultraspere ODS (5 μm) Altex (Beckman) 4.6 mm (i.d.)×250 mm
  pre-column: Brownlee Labs. RP 18 (5 μm)

| eluent A: | CH$_3$CN | 10% | adjusted |
| | (2.5 g/l) NaH$_2$PO$_4$.H$_2$O | 90% | at pH 6.0 |
| eluent B: | CH$_3$CN | 70% | adjusted |
| | (2.5 g/l) NaH$_2$PO$_4$.H$_2$O | 30% | at pH 6.0 | elution: linear gradient from 5% to 60% of eluent B in eluent A, in 40 min
  flow rate: 1.6 ml/min
  U.V. detector: 254 nm
  internal standard: antibiotic L 17054 (TA3-1) (Gruppo Lepetit S.p.A.)
(E) $R_f$ value of 0.39 in the following chromatographic system:
  1 M NaCl containing 5 g/l of NaH$_2$PO$_4$.H$_2$O: 70
  acetonitrile: 30
  adjusted to pH 6.0, using silanized silica gel 60 F$_{254}$ Merck plates (layer thickness 0.25 mm,
  Visualization:
    U.V. light
    Yellow color with Pauly Reagent, i.e. diazotized sulfanilic acid (J. Chromatog. 20, 171 (1965), Z. Physiol Chem. 292, 99, (1953))
    Bioautography using B. subtilis ATCC 6633 on minimal Davis medium.
(F) A fast atom bombardment (FAB) mass spectrum with M+H$^\oplus$ at about 1374.

On the basis of the physico-chemical characteristics and by reference to the structure of known antibiotic substances of the same class, the above formula I wherein A represents hydrogen and B represents mannosyl can be attributed to antibiotic A 40926 mannosyl aglycon.

In the present description and claims, the term "antibiotic A 40926 mannosyl aglycon" is intended to encompass the "internal salt" form as well as the possible acid and basic addition salts.

Antibiotic A 40926 mannosyl aglycon is prepared by hydrolizing antibiotic A 40926 complex enriched in factor A and factor B, antibiotic A 40926 factor A, factor B, factor B$_0$ or mixtures thereof under controlled acidic conditions.

These controlled acid conditions are represented by a concentrated aqueous solution of a mineral or organic strong acid optionally in the presence of an aprotic organic solvent. Preferred examples of strong mineral acids are sulfuric and phosphoric acid.

A preferred strong organic acid is trifluoroacetic acid.

Preferred aprotic organic solvents are alicyclic or cyclic alkyl ethers such as dioxane and tetrahydrofuran, lower alkyl sulfoxides such as dimethylsulfoxide and lower alkyl amides such as dimethylformamide.

The reaction temperature is generally kept between 0° C. and the reflux temperature of the reaction mixture. In many instances it is between 20° C. and 55° C. and most preferably it is room temperature.

The reaction time varies depending on the specific reaction parameters and since the reaction course may followed by TLC or HPLC techniques, the man skilled in the art is capable of monitoring the reaction course and deciding when the reaction may be considered complete.

A preferred embodiment of the process of the invention is represented by the controlled hydrolysis antibiotic A 40926 complex or a pure factor thereof to give antibiotic A 40926 mannosyl aglycon in the presence of aqueous 80–95% trifluoroacetic acid at room temperature.

Another preferred embodiment of the process of the invention is represented by the controlled hydrolysis of antibiotic A 40926 mannosyl aglycon in the presence of a mixture 2:1 to 1:2 of aqueous 1–2N sulfuric acid and dioxane.

The purification of crude antibiotic A 40926 mannosyl aglycon as recovered at the end of the hydrolysis step may be accomplished according to known per se techniques, such as precipitation by addition of non-solvents, extraction with solvents and chromatography.

Preferred chromatographic procedures includes column chromatography and the most preferred chromatographic procedure is reverse-phase coluumn chromatography.

A suitable reverse-phase liquid chromatography procedure, preferably employes stainless steel colums (100-200 bar). The solid phase may be a silanized silica gel with a hydrocarbon phase at (2-18) carbon atoms (most preferably C 18) or phenyl group, and the eluent is a mixture of a polar water-miscible solvent and an aqueous buffer at a pH compatible with the resin (preferably pH 3-8).

Representative examples of polar water-miscible solvents are: water-soluble alcohols, (such as methanol, ethanol, iso-propanol, n-butanol), acetone, acetonitrile, lower alkyl alkanoates (such as ethyl acetate), tetrahydrofuran, dioxane and dimethylformamide and mixtures thereof; the preferred polar water-miscible solvent being acetonitrile.

The eluted fractions are assayed for their antibiotic content by means of the usual bioassays, such as paperdisc or agar-diffusion assays, on susceptible microorganisms. Examples of susceptible organisms are *Bacillus subtilis* and *S. aureus*.

The purification as well as the reaction are also conveniently monitored by TLC or HPLC techniques.

A preferred HPLC technique is represented by a reverse-phase HPLC using a column of porous and spheric particles of silanized silica gel functionalized with C-18 alkyl groups having a diameter preferably of 5 micrometers (such as 5 μm Ultrasphere ® ODS Altex; Beckman Co.), a pre-column which is a silica gel functionalized with C-18 alkyl groups (such as RP 18 Brownlee Labs) and an eluent which is a linear gradient mixture of a polar water miscible solvent, such as one of those described above, in an aqueous buffered solution.

Preferably this solution is adjusted to pH 5-7. A most preferred eluent is represented by a linear gradient from 5 to 60% of eluent B in eluent A wherein eluent A is a mixture of acetonitrile/aqueous buffer, pH 5-7, 10:90 and eluent B is a mixture of acetonitrile/aqueous buffer, pH 5-7, 70:30. As known in the art, many substances can be used as internal standards. A very convenient one is, in this case, antibiotic L 17054 which has a retention time close to the compounds of the invention in this HPLC system. This standard substance is known and has been described in European Patent Application Publication No. 0119575.

The antibacterial activity of the compound of the invention can be demonstrated in vitro by means of standard dilution tests on different microorganism cultures.

Culture media and growth conditions for MIC (minimal inhibitory concentration) determinations were as follows: Isosensitest broth (Oxoid), 24 h, for staphylococci, Strep. faecalis and Gram-negative bacteria (Escherichia coli); Todd-Hewitt broth (Difco), 24 h for other streptococcal species; GC base broth (Difco)+1% Isovitalex (BBL), 48 h, $CO_2$-enriched atmosphere for Neisseria gonorrhoeae; GB base agar (Difco)+1% Isovitalex+0.001% hemin, 24 h for Haemophilus influenzae; AC broth (Difco), 24 h, anaerobic atmosphere for Clostridium perfringens; Wilkins-Chalgren agar (ref: T. D. Wilkins & S. Chalgren, 1976, Antimicrob. Ag. Chemother. 10, 926), 48 h, anaerobic atmosphere for the other anaerobes (C. difficile, Propionibacterium acnes, Bacteroides fragilis); PPLO broth (Difco)+10% horse serum+1% glucose, 48 h for Mycoplasma gallisepticum. Incubation was at 37° C. Inocula were as follows: 1% (v/v) cf a 48 h broth culture for M. gallisepticum; about $10^4$–$10^5$ colony-forming units/ml for other broth dilutior MICs; about $10^4$–$10^5$ bacteria/spot (inoculated with a multipoint inoculator) for agar dilution MICs (H. influenzae, C. difficile, P. acnes, B. fragilis).

The minimal inhibitory concentrations (MIC, $\mu g/ml$) on some microorganisms are reported below in Table I.

TABLE I

| Strain | Antibiotics A 40926 mannosyl aglycon M.I.C. ($\mu g/ml$) |
| --- | --- |
| Staph. aureus Tour | 0.25 |
| Staph. aureus Tour (L165) $10^6$ cfu/ml | 1 |
| Staph. aureus Tour 30% bovine serum | 2 |
| Staph. epidermidis ATCC 12228 | 0.5 |
| Strep. pyogenes C203 | 1 |
| Strep. pneumoniae UC41 | 1 |
| Strep. faecalis ATCC 7080 | 1 |
| Strept. mitis clin. isolate | 1 |
| Clostridium perfringens ISS30543 | 0.13 |
| Clostridium difficile ATCC 9689 | 2 |
| Bacteroides fragilis ATCC 23745 | 64 |
| Propionibacterium acnes ATCC 6919 | 1 |
| Neisseria gonorrhoeae ISM68/126 | 32 |
| Haemophilus influenzae type b ATCC 19418 | 64 |
| Escherichia coli SKF 12140 | >128 |
| Mycoplasma gallisepticum S6 Weybridge | >128 |

The antimicrobial activity of the compound of the invention is confirmed also in in vivo experiments conducted essentially as described by R. Pallanza et al., J. Antimicrob. Chemother. 11, 419 (1983).

The experimental infection was induced in mice by intraperitoneally administering a suspension of S. pyogenes C 203. Inocula had been adjusted so that the untreated animals died of septicemia within 48 h. Animals were treated subcutaneously with the test compound about 30 min after infection.

The $ED_{50}$ value was calculated on the 10th day by the method of Spearman and Karber (D. J. Finney "Statistical Methods in Biological Assay", Griffin, page 524, 1952) on the basis of the percentage of survival at each dose.

In the above conditions the $ED_{50}$ for antibiotic A 40926 mannosyl aglycon was 3.8 mg/kg.

Antibiotic A 40926 mannosyl aglycon possesses acid and basic functions and can form salts according to conventional procedures.

Representative and suitable acid addition salts of the compounds of the invention include those salts formed by standard reaction with both organic and inorganic acids such as, for example, hydrochloric, hydrobromic, sulfuric, phosphoric, acetic trifluoroacetic, trichloroacetic, succinic, citric, ascorbic, lactic, maleic, fumaric, palmitic, cholic, pamoic, mucic, glutamic, camphoric, glutaric, glycolic, phthalic, tartaric, lauric, stearic, salicylic, methanesulfonic, benzenesulfonic, sorbic, picric, benzoic, cinnamic and the like acids.

Representative examples of these bases are: alkali metal or alkaline-earth metal hydroxide such sodium, potassium, and calcium, hydroxide; ammonia and organic amines aliphatic, alicyclic or aromatic such as methylamine, dimethylamine, trimethylamine, and picoline.

The transformation of the free amino or nor-salt compounds of the invention into the corresponding addition salts, and the reverse, i.e. the transiormation of an addition salt of a compound of the invention into the non-salt or free amino form, are within the ordinary technical skill and are encompassed by the present invention.

For instance antibiotic A 40926 mannosyl aglycon can be transformed into the corresponding acid or base addition-salt by dissolving the non-salt form in an aqueous solvent and adding a slight molar excess of the selected acid or base. The resulting solution or suspension is then lyophilized to recover the desired salt.

In case the final salt is unsoluble in a solvent where the non-salt form is soluble it is recovered by filtration from the organic solution of the non-salt form after addition of the stoichiometric amount or a slight molar excess of the selected acid or base. The non-salt form can be prepared from a corresponding acid or base salt dissolved in an aqueous solvent which is then neutralized to free the non-salt form.

When following the neutralization desalting is necessary, a common desalting procedure may be employed. For example, column chromatography on silanized silica gel, non-functionalized polystyrene, acrylic and controlled pore polydextrane resins (such as Sephadex LH 20) or activated carbon may be conveniently used. After eluting the undesired salts with an aqueous solution, the desired product is eluted by means of a linear gradient or a step-gradient of a mixture of water and a polar or apolar organic solvent, such as acetonitrile/water from 50:50 to about 100% acetonitrile.

As it is known in the art, the salt formation either with pharmaceutically acceptable acids (bases) or non-pharmaceutically acceptable acids (bases) may be used as a convenient purification technique. After formation and isolation, the salt form of an A 40926 antibiotic can be transformed into the corresponding non-salt or into a pharmaceutically acceptable salt.

In some instances, the base addition salt of antibiotic A 40926 mannosyl aglycon is more soluble in water and hydrophilic solvents.

Antibiotic A 40926 mannosyl aglycon is active against gram-positive bacteria which are responsible for many widely diffused infections. Because of the increasing resistance of these pathogens to the usual therapeutic treatments, the need for new antibiotic substances is still great.

In general for antibacterial treatment antibiotic A 40926 mannosyl aglycon as well as the non-toxic pharmaceutically acceptable salts thereof or mixture thereof, can be administered by different routes such as topically or parenterally. The parenteral administration is, in general, the preferred route of administration.

Compositions for injection may take such forms as suspensions, solutions, or emulsions in oily or aqueous vehicles, and may contain adjuvants such as suspending, stabilizing and/or dispersing agents.

Alternatively, the active ingredient may be in powder form for reconstitution at the time of delivery when a suitable vehicle, such as sterile water, is added thereto.

Depending on the route of administration, these compounds can be formulated into various dosage forms.

In some instances, it may be possible to formulate the compounds of the invention in enteric-coated dosage forms for oral administration which may be prepared as known in the art (see for instance "Remington's Pharmaceutical Sciences", fifteenth edition, Mack Publishing Company, Easton, Pa., USA, page 1614).

This could be especially the case when the absorption of the antimicrobial substance in the enteric tract is particularly desired while passing unaltered through the gastric tract.

The amount of active principle to be administered depends on various factors such as the size and condition of the subject to be treated, the route and frequency of administration, and the causative agent involved.

The antibiotic substance of the present invention, namely antibiotic A 40926 mannosyl aglycon and the physiologically acceptable salts thereof, are generally effective at a daily dosage of between about 0.5 and 50 mg of active ingredient per kilogram of patient body weight, optionally divided into 1 to 4 administrations per day.

Particularly desirable compositions are those prepared in dosage units containing from about 100 to about 5,000 mg per unit.

Sustained-action formulations can be prepared based on different mechanisms and methods, as known in the art.

A preferred method for preparing a sustained-action formulation containing antibiotic A 40926 mannosyl aglycon, involves the use of a water insoluble form of this antibiotic suspended in an aqueous or oily medium.

Preparation of pharmaceutical compositions

A unit dosage form for intramuscular injection is prepared with 5 ml of sterile suspension USP containing 8% propylene glycol and 1,000 mg of antibiotic A 40926 mannosyl aglycon.

A unit dosage form for intramuscular injection is prepared with 5 ml of sterile water USP containing 500 mg of antibiotic A 40926 mannosyl aglycon A unit dosage form for intramuscular injection is prepared with 2,000 mg of antibiotic A 40926 mannosyl aglycon sodium salt suspended in 5 ml of sterile water for injection.

Furthermore, the antibiotic substance of tha invention is useful for suppressing the growth of *Clostridium difficile* which causes pseudomembranous colitis in the intestine. The antibiotic could be used in the treatment of pseudomembranous colitis by the oral administration of an effective dose of the antibiotic or a pharmaceutically-acceptable salt thereof, prepared in a pharmaceutically-acceptable dosage form. For such use, the antibiotic can be administered in gelatin capsules or in liquid suspension.

Besides their activity as medicaments, antibiotic A 40926 mannosyl aglycon and the pharmaceutically acceptable salts thereof, can be used as animal growth promoters.

For this purpose, a compound of the invention is administered orally in a suitable feed. The exact concentration employed is that which is required to provide for the active agent in a growth promotant effective amount when normal amounts of feed are consumed.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed.

The way in which such feed premixes and complete rations can be prepared and administered are described in reference books (such as "Applied Animal Nutrition", W. H. Freedman and CO., S. Francisco, USA, 1969 or "Livestock Feeds and Feeding" O and B books, Corvallis, Ore., USA, 1977) and are incorporated herein by reference.

The following Examples further illustrate the invention and, as such, should not be construed as limiting its scope.

EXAMPLE 1

(a) A sample (214 mg) of antibiotic A 40926 complex AB (see Preparation 3, below) is dissolved in a trifluoroacetic acid/water 9/1 (v/v) mixture (30 ml). After 48 h at room temperature the mixture is evaporated under vacuum at room temperature to 1/10 of the original volume, rinsed with 30 ml of water and then extracted twice with ethyl acetate. The aqueous phase contained mainly the A 40926 mannosyl aglycon and trifluoroacetic acid.

(b) This aqueous phase is neutralized with 1N sodium hydroxide and then loaded on a column (bed height 5 cm) of silanized silica gel 60, 70–230 mesh (50 ml; Merck Co. art. 7719) in water. The column is washed with distilled water and then eluted with acetonitrile-water 1/1 (v/v).

Fractions of 20 ml are collected, analyzed by HPLC (or TLC) and those containing antibiotic A 40926 mannosyl aglycon are pooled, concentrated to a small volume by azeotropic distillation with n-butanol and then freeze-dried to give 124 mg of antibiotic A 40926 mannosyl aglycon.

EXAMPLE 2

The same procedure of Example 1 is repeated but the starting material is reacted with the aqueous trifluoroacetic acid for 2 h at about 65° C. instead of at room temperature overnight. Yield 110 mg of final product.

EXAMPLE 3

The same procedure of Example 1 is repeated but using a mixture of 2N aqueous sulfuric acid and dioxane (one to one ratio) instead of aqueous trifluorozcetic acid. The reaction temperature is, in this case, about 65° C., overnight. The yields are similar to those obtained in the foregoing examples.

EXAMPLE 4

The procedure of Example 1 is repeated using
(a) antibiotic A 40926 factor A
(b) antibiotic A 40926 factor B as the starting materials instead of antibiotic A 40926 complex. The yields are similar to those obtained in the foregoing examples.

EXAMPLE 5

Antibiotic A 40926 mannosyl aglycon as obtained according to the procedure of Example 1a is further purified as follows: the aqueous phase is neutralized with 1N aqueous sodium hydroxide and then concentrated to about 18 ml under vacuum.

The obtained solution is applied in two subsequent chromatographic runs to a stainless steel column (2 cm diameter) packed with 20 g of 10 micron RP 18 silica gel (Lichrosorb RP18 Merck Co., art. 9334) equilibrated with a solvent consisting of acetonitrile: 18 mM sodium phosphate buffer pH 6.0, 17:83 (v/v).

The column is part of a Chromatospac Modulprep unit. (Joben Yvon, 16–18 Rue du Canal 91160, Lorgjnneau, France). The column is eluted with acetonitrile: 18 mM sodium phosphate buffer pH 6.0, 17:83 (v/v). The eluted fractions are monitored at 275 nm using a UVICORD S UV monitor (LKB Co.) and are analyzed by HPLC and TLC.

The fractions of the two chromatographic runs containing antibiotic A 40926 mannosyl aglycon are pooled and concentrated under vacuum to remove the organic solvent. The resulting aqueous solution is then chromatographed and worked up as described in Example 1b giving 66 mg of A 40926 mannosyl aglycon lyophilizate.

Preparation of the starting materials

Preparation 1

Fermentation of Actinomadura sp. ATCC 39727

A culture of antibiotic A 40926 producing strain (Actinomadura sp. ATCC 39727) is grown on oatmeal agar slant for 2–3 weeks at 28° C. and used to inoculate a 500 ml Erlenmeyer flask containing 100 ml of medium composed of 0.5% meat extract, 0.5% autolyzed yeast, 0.5% peptone, 0.3% casein hydrolyzed, 2% glucose, 0.15% NaCl (pH 7.5 before sterilization).

The flask is incubated at 28° C. on a rotary shaker at 200 rpm for about 72 h and then the culture is transferred to a fermentor containing 4 l of the above medium. This culture is grown at 28° C. for about 72 h with air-flow of about two liters per minute and stirring at about 900 rpm. Then, it is used to inoculate a 200 l fermentor of the same medium. This fermentor is aerated with 100 l per minute of sterile air and is stirred at 250 rpm at about 28° C. The antibiotic production is monitored by the paper-disc agar diffusion method using B. subtilis on a minimal medium as the test organism. The maximum activity is obtained after 72–96 h.

Preparation 2

Recovery of antibiotic A 40926

(A) The fermentation broth is cooled to 4° C., brought to pH 9.5 and stirred. After about 1 h it is filtered and the filtrate is adjusted to pH about 3.5 with an aqueous mineral acid. The mixture is stirred for 30 min at 4° C. and then filtered with (Hyflo-FloMa ®) filter aid. The clear filtrate is discharged and the filter cake is suspended in deionized water, adjusted to pH about 8.5, stirred and then filtered. The recovered cake is subjected to the same procedure. The pooled filtrates contain antirbiotic A 40926.

(B) Swollen D-Ala-D-Ala-ε-aminocaproyl-Sepharose modified matrix (2 l) is added to the fermentation broth obtained according to Preparation 1 (after filtering it and bringing the pH of the clear filtrate to about 8.5) or to the pooled filtrate obtained according to the above Preparation 2 A.

After stirring overnight at room temperature, the resin is recovered by filtration and is washed sequentially with about 2×10 l of 0.45 mM HCl-TRIS buffer pH 7.5 (TRIS=2-amino-2-hydroxymethyl-1,3-propanediol) which contains 5% (w/v) NaCl and then with distilled water (4×20 l). The A 40926 antibiotic is eluted from the resin with 1% (w/v) ammonia hydrate (2×20 l). The eluates are left overnight at room temperature and then concentrated to a small volume (about 2.5 l). Water is eliminated by azeotropical distillation with n-butanol. Petroleum ether is then added, precipitating 3.4 g of crude antibiotic A 40926 complex.

Preparation 3

Purification of antibiotic A 40926 complex AB

Crude antibiotic A 40926 complex obtained essentially following the procedure of the above Preparation 2, (750 mg; HPLC titre 70%) is dissolved in 400 ml of water, adjusted to pH 7.5 and filtered. The filtrate is then subjected to affinity chromatography on a D-Ala-D-Ala-ε-aminocaproyl-Sepharose column (50 ml of swollen resin; bed height=5 cm). The column, equilibrated with 0.16% (w/v) ammonia containing 2M NaCl adjusted to pH 7.5 with HCl, is developed sequentally with the following three buffer solutions:

buffer A: 0.16% (w/v) ammonia contaning 2M NaCl adjusted to pH 7.5 with HCl, (2.6 column bed volumes);

buffer B: 0.16% (w/v) ammonia containing 2M NaCl adjusted to pH 9.5 with HCl (16 columr bed volumes);

buffer C: 1% (w/v) aqueous ammonia pH 11.4 (2.6 column bed volumes).

Buffer C elutes antibiotic A 40926 complex AB in a single fraction. This eluted fraction is adjusted to pH 7.0 and reapplied to the same affinity column buffered with with 10 mM TRIS-HCl pH 7.0. The column is washed with distilled water until desalting is complete. The antibiotic is then eluted with 2 column bed volumes of 0.39% (w/v) aqueous ammonia pH 11.0.

The eluted fractions are concentrated to a small aqueous mixture and then freeze-dried. Pure antibiotic A 40926 complex AB (374 mg) is obtained.

Preparation 4

Isolation of antibiotic A 40926 factor A and B (A) Antibiotic A 40926 complex as obtained according to Preparation 2 (3.3 g) or antibiotic A 40926 complex AB as obtained according to Preparation 3 (2.3 g) is suspended in 0.5 l of water, stirred and then filtered. The clear filtrate is applied to a silanized silica gel column (200 g; bed h 18 cm; silanized Silicagel 60; 70–230 mesh, Merck Inc.) pre-equilibrated with solution A (0.001M aqueous sodium EDTA containing 0.25% (w/v) NaH$_2$PO$_4$. H$_2$O and 2.5% (w/v) NaCl adjusted to pH 6.0 with NaOH). The column is eluted with a linear gradient from 0% to 40% (v/v) of acetonitrile in solution A with a total volume of about 7 l in about 48 h. Fractions of about 15.5 ml are collected and assayed by bioassay on Bacillus subtilis and analyzed by HPLC. Fractions having a similar antibiotic content are pooled.

Fractions No. 310–330 and No. 348–365 contained the antibiotic substances denomirated, respectively, A 40926 factor A and A 40926 factor B.

(B) The pooled fractions containing the single A 40926 factors A and B are concentrated under reduced pressure to remove acetonitrile, diluted with water (about twice the volume of the initial solutions) and applied to a silanized silica gel coluxn of the type described above (volume of the swollen matrix: 50 ml; bed height of 15 cm). The column is washed with deionized water until desalting is complete and finally developed with acetonitrile/water 60:40 (v/v).

The eluted fractions are concentrated under reduced pressure and the residues are freeze-dried to obtain 134 mg of antibiotic A 40926 factor A from the first group of eluted fractions (fractions 310–330 above) and 206 mg of A 40926 factor B from the second group of eluted fractions (fractions 348–365, above).

Preparation 5

Isolation of antibiotic A 40926 factor PA and factor PB

By essentially following the procedure of Preparation 2A and the first steps of the procedure of Preparation 2B, the antibiotic linked to the resin is eluted with 1% (w/v) ammonia hydrate (2×20 l). The eluates are adjusted to pH 7.8 with sulfuric acid and concentrated to a small volume under vacuum by azeotropical distillation with n-butanol to obtain an aqueous concentrate which is then filtered on paper. The recovered filtrate contains antibiotic A 40926 factor PA, A 40926 factor PB and minor amounts of A 40926 factor A and factor B (HPLC).

A sample (10 ml) of this aqueous concentrate containing about 50 mg/ml of pure antibiotic A 40926 complex (HPLC analysis) is filtered on 5 micrometer pore-size filter (Acrodis ®; Gelman Science Inc.) and then applied to a stainless steel column (diameter=2 cm) containing 20 g of an octadecyl silyl reverse-phase silica gel (Lichrisorb RP 18, Merck Inc.; particle size 10 μm). The silica gel is then packed under moderate pressure (nominal pressure about 14 bar) in a stainless steel column of a Chromatospac Modulprep apparatus (Joben Yvon, France) and equilibrated with a mixture consisting of acetonitrile and 18 mM sodium phosphate buffer pH 6.0), 25:75 (v/v). The elution is carried out using the same solvent mixture used for the equilibration at a flow rate of about 10.5 ml/min. The eluate is monitored by bioassay on *Bacillus subtilis* and by HPLC.

Those fractions having similar antibiotic content are pooled and the homogeneous fractions of 5 chromatographic runs are concentrated to evaporate the organic solvent.

The resulting solution is diluted with aqueous 1M sodium chloride to twice the original volume and is applied to a silanized silica gel column (50 g; bed height 5 cm; Silanized silica gel 60; Merck Inc.) equilibrated with water.

The column is washed with deionized water until desalting is complete (no AgCl precipitation in the eluates after addition of aqueous AgNO$_3$) and then eluted with acetonitrile:water 1:1 (v/v). The eluates having similar antibiotic content (HPLC analysis) are pooled, concentrated to a small volume by azeotropical distillation with n-butanol to obtain an aqueous phase which is then freeze-dried. Yields:

| antibiotic A 40926 factor PA | 55 mg |
| antibiotic A 40926 factor PB | 51 mg |
| antibiotic A 40926 factor A | 38 mg |
| antibiotic A 40926 factor B$_0$ | 33 mg |

Preparation 6

Transformation of antibiotic A 40926 factor PA and antibiotic A 40926 factor PB into antibiotic A 40926 factor A and factor B, respectively Antibiotic A 40926 factor PA and antibiotic A 40926 factor PB (50 mg) are separately dissolved in 2.5 ml of aqueous 1% (w/v) NH$_4$OH and the resulting solutions are kept for about 24 h at room temperature with stirring.

Antibiotic A 40926 factor A is obtained from the solution originally containing antibiotic A 40926 factor PA, and antibiotic A 40926 factor B is obtained from the solution originally containing antibiotic A 40926 factor PB by removing water by azeotropic distillation with n-butanol, precipitating with ethyl ether and collecting the precipitate by filtration (yield about 75%).

Preparation of D-Ala-D-Ala-Sepharose

Activated CH-Sepharose 4B (Pharmacia Fine Chemicals) (1 g) is swollen for 15 minutes in 1 mM cold ice hydrochloric acid and washed with the same solution.

The obtained gel (about 3 ml) is mixed with a solution of D-alanyl-D-alanine (30 mg) in 0.5M sodium chloride and 0.1M sodium bicarbonate buffer at pH 8.

The mixture is rotated end-over-end for 1 hour at room temperature.

After the coupling reaction is completed, the ligand excess is washed off with the buffer. The unlinked activated groups of the dextrane support are blocked by treating them with 1M ethanolamine hydrochloride at pH 9 for 1 hour.

Then the Sephadex-ϵ-aminocaproyl-D-alanyl-D-alanine modified matrix is recovered by filtration and thoroughly washed alternatively with 0.5M sodium chloride and 0.1M sodium acetate pH 4, and with 0.5M sodium chloride and 0.1M tris(hydroxymethyl)aminomethane buffer pH 8. (four times).

We claim:

1. Antibiotic A 40926 mannosyl aglycon and the addition salts thereof which has the following characteristics, in the non-addition salt form:

(A) ultraviolet absorption spectrum which exhibits the following absorption maxima:

| | | λ max (nm) |
|---|---|---|
| (a) | 0.1 N HCl | 280 |
| (b) | phosphate buffer pH 7.38 | 280 |
| | | 300 (shoulder) |
| (c) | 0.1 N potassium hydroxide | 298 |
| (d) | phosphate buffer pH 9.0 | 282 |
| | | 300 (shoulder) |

(B) infrared absorption spectrum which exhibits the following absorption maxima (cm$^-$): 3700–3100; 3000–2800 (nujol); 1655; 1620–1540; 1505; 1460 (nujol); 1375 (nujol) 1350–1250; 1210; 1150; 1020; 970; 850, 810

(C) $^1$H-NMR spectrum which exhibits the following groups of signals (in ppm) at 270 MHz recorded in DMSO d$_6$ (hexadeuterodimethylsulfoxide) plus CF₃COOH using TMS as the internal standard (0.00 ppm), (δ=ppm, multiplicity, attributions): 2.51, s (DMSOd$_5$); 2.50, s (NCH$_3$); 2.88, m (Z2); 3.30, m (Z'2); 4.08, m (X6); 4.44, d (X5); 4.49, d (X7); 4.83, m (X2); 5.02, s (4F); 5.08, s (Z6); 5.31, s (anomeric proton of mannose); 5.53, d (X4); 5.78, s (4B); 6.08, d (X3); 7.70, s (6B); 6.44–8.52 (aromatic and peptidic NH's)

(D) retention-time ($R_t$) of 1.18 relative to antibiotic L 17054 (TA3-1) ($R_t$=8.78 min), when analyzed by reverse phase HPLC under the following conditions:
column: Ultraspere ODS (5 μm) Altex (Beckman) 4.6 mm (i.d.)×250 mm
pre-column : Brownlee Labs. RP 18 (5 μm)

| eluent A: | CH$_3$CN | 10% | adjusted |
|---|---|---|---|
|  | (2.5 g/l) NaH$_2$PO$_4$.H$_2$O | 90% | at pH 6.0 |
| eluent B: | CH$_3$CN | 70% | adjusted |
|  | (2.5 g/l) NaH$_2$PO$_4$.H$_2$O | 30% | at pH 6.0 | elution: linear gradient from 5% to 60% of eluent B in eluent A, in 40 min
flow rate: 1.6 ml/min
U.V. detector: 254 nm
internal standard: antibiotic L 17054 (TA3-1) (Gruppo Lepetit S.p.A.)

(E) Rf value of 0.39 in the following chromatographic system:

| 1 M NaCl containing 5 g/l of NaH$_2$PO$_4$.H$_2$O | 70 |
|---|---|
| acetonitrile | 30 |
| adjusted to pH 6.0, using silanized silica gel | 60 |
| F$_{254}$ Merck plates (layer thickness 0.25 mm) | |

Visualization:
U.V. light
Yellow color with Pauly Reagent, i.e. diazotized sulfanilic acid (J. Chromatog. 20, 171 (1965), Z. Physiol. Chem. 292, 99, (1953))
Bioautography using B. subtilis ATCC 6633 on minimal Davis medium.

(F) A fast atom bombardment (FAB) mass spectrum with M+H⊕ at about 1374.

2. Antibiotic A 40926 mannosyl aglycon and the addition salts thereof, which have the following formula, in the non-addition salt form:

wherein
A represents hydrogen, and
B represents mannosyl.

3. A composition comprising an antibiotic of claim 1 or 2 in admixture with a pharmaceutically acceptable carrier.

4. A method for the treatment of bacterial infections of susceptible organisms, comprising administering to a patient in need thereof, an antibacterial quanitity of an antibiotic of claim 1 or 2.

* * * * *

UNITED STATES PATENT AND TRADEMARK OFFICE
CERTIFICATE OF CORRECTION

PATENT NO. : 4,782,042

DATED : November 1, 1988

INVENTOR(S) : Enrico Selva, et al.

It is certified that error appears in the above-identified patent and that said Letters Patent is hereby corrected as shown below:

On the cover page, in the Abstract at line 5, the patent reads "infectious disease" and should read --infectious diseases--. At column 3, line 26, the patent reads "0.25 mm," and should read --0.25 mm)--. At column 3, line 64, the patent reads "In many instances it is between 20°C and 55°C and most", and should read --In many instances it is between 15°C and 75°C, while a preferred temperature is between 20°C and 55°C and most--,. At column 3, line 67-68, the patent reads "may followed" and should read --may be followed--. At column 4, line 5, the patent reads "hydrolysis antibiotic" and should read --hydrolysis of antibiotic--. At column 4, line 22, the patent reads "coluumn" and should read --column--. At column 4, lines 25-26, the patent reads "employes stainless steel colums (100-200 bar)" and should read --employs stainless steel columns under moderate pressure (5-50 bar) or at high pressure (100-200 bar)--.

At column 5, line 22, the patent reads "(v/v) cf" and should read --(v/v) of--. At column 5, line 24, the patent reads "dilutior" and should read --dilution--.

At column 5, line 32, in Table I, the patent reads "Antibiotics" and should read --Antibiotic--. At column 7, line 52, the patent reads "mannosyl aglycon" and should read --mannosyl aglycon.--. At column 7, line 57, the patent reads "tha" and should read --the--. At column 9, line 18, the patent reads "Lorgjnneau" and should read --Longjnneau--. At column 9, line 68, the patent reads "antirbiotic" and should read --antibiotic--.

UNITED STATES PATENT AND TRADEMARK OFFICE
CERTIFICATE OF CORRECTION

PATENT NO. : 4,782,042

DATED : November 1, 1988

INVENTOR(S) : Enrico Selva, et al.

It is certified that error appears in the above-identified patent and that said Letters Patent is hereby corrected as shown below:

```
At column 10, line 31, the patent reads "sequentally" and
should read --sequentially--.  At column 10, line 33, the
patent reads "contaning' and should read --containing--.  At
column 10, line 37, the patent reads "columr" and should read
--column--.  At column 10, lines 43-44 , the patent reads
"buffered with with 10 mM" and should read --buffered with 10
mM".  At column column 11, line 2, the patent reads
"denomirated," and should read --denominated--.  At column 11,
line 8, the patent reads "coluxn" and should read --column--.
At column 11, line 38, the patent reads "Acrodis" and should
read --Acrodisc--.  At column 12, line 62, the patent reads
"(cm-):" and should read --(cm-1):.
```

Signed and Sealed this

Twenty-seventh Day of June, 1989

Attest:

DONALD J. QUIGG

Attesting Officer

Commissioner of Patents and Trademarks